US009579462B2

(12) United States Patent
Crank

(10) Patent No.: US 9,579,462 B2
(45) Date of Patent: *Feb. 28, 2017

(54) NEEDLELESS INJECTION DEVICE COMPONENTS, SYSTEMS, AND METHODS

(71) Applicant: Astora Women's Health Holdings, LLC, Minnetonka, MN (US)

(72) Inventor: Justin M. Crank, Maple Grove, MN (US)

(73) Assignee: Astora Women's Health Holdings, LLC, Minnetonka, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/493,598

(22) Filed: Sep. 23, 2014

(65) Prior Publication Data

US 2015/0011966 A1 Jan. 8, 2015

Related U.S. Application Data

(63) Continuation of application No. 13/133,125, filed as application No. PCT/US2009/006384 on Dec. 4, 2009, now Pat. No. 8,852,142.

(60) Provisional application No. 61/139,974, filed on Dec. 22, 2008, provisional application No. 61/122,808, filed on Dec. 16, 2008, provisional application No. 61/122,793, filed on Dec. 16, 2008.

(51) Int. Cl.
*A61M 5/30* (2006.01)
*A61M 25/00* (2006.01)
*A61M 25/10* (2013.01)

(52) U.S. Cl.
CPC ........... *A61M 5/30* (2013.01); *A61M 25/0069* (2013.01); *A61M 25/1025* (2013.01)

(58) Field of Classification Search
CPC . A61M 5/30; A61M 25/0069; A61M 25/1025
USPC .......................................................... 604/68
See application file for complete search history.

(56) References Cited

U.S. PATENT DOCUMENTS 2,607,342 A 11/1950 Abel
3,402,718 A 9/1968 Doherty
(Continued)

FOREIGN PATENT DOCUMENTS

WO    WO 96/16606    6/1996
WO    WO 97/36625    10/1997
(Continued)

*Primary Examiner* — Theodore Stigell
(74) *Attorney, Agent, or Firm* — Kagan Binder, PLLC

(57) ABSTRACT

Needleless injection device components, systems, and methods that involve features including an elongate shaft that has a working shaft comprising a working shaft proximal end, a working shaft distal end, and a working lumen extending between the working shaft proximal end and the working shaft distal end, an injection shaft including an injection shaft proximal end, an injection shaft distal end, and a needless injection orifice disposed through the sidewall at the injection shaft distal end, the injection shaft moveably disposed within the working lumen, and a tissue tensioner secured to the injection shaft at the injection shaft distal end and moveable relative to the working lumen, the tissue tensioner having an expandable surface capable of exhibiting an expanded state and a non-expanded state, the tissue tensioner in the expanded state being capable of tensioning luminal tissue for injection by the needless injection orifice.

20 Claims, 9 Drawing Sheets

(56) References Cited

U.S. PATENT DOCUMENTS

| | | |
|---|---|---|
| 3,714,943 A | 2/1973 | Yanof et al. |
| 4,093,108 A | 6/1978 | Hein et al. |
| 4,130,119 A | 12/1978 | Sessions et al. |
| 4,742,817 A | 5/1988 | Kawashima et al. |
| 4,946,442 A | 8/1990 | Sanagi |
| 5,007,897 A | 4/1991 | Kalb et al. |
| 5,116,313 A | 5/1992 | McGregor |
| 5,261,889 A | 11/1993 | Laine et al. |
| 5,336,178 A | 8/1994 | Kaplan et al. |
| 5,693,016 A | 12/1997 | Gumaste et al. |
| 5,840,062 A | 11/1998 | Gumaste et al. |
| 6,203,533 B1 | 3/2001 | Ouchi |
| 6,210,378 B1 | 4/2001 | Ouchi |
| 6,238,336 B1 | 5/2001 | Ouchi |
| 6,280,413 B1 | 8/2001 | Clark et al. |
| 6,344,027 B1 | 2/2002 | Goll |
| 6,400,980 B1 | 6/2002 | Lemelson |
| 6,488,659 B1 | 12/2002 | Rosenman |
| 6,537,205 B1 | 3/2003 | Smith |
| 6,547,767 B1 | 4/2003 | Moein |
| 6,641,553 B1 | 11/2003 | Chee et al. |
| 6,685,669 B2 | 2/2004 | Bellhouse et al. |
| 6,905,475 B2 * | 6/2005 | Hauschild ........ A61B 17/32037 604/506 |
| 7,594,900 B1 | 9/2009 | Nash et al. |
| 7,749,156 B2 | 7/2010 | Ouchi |
| 8,852,142 B2 * | 10/2014 | Crank ............ A61M 5/30 604/68 |
| 9,295,823 B2 * | 3/2016 | Rykhus, Jr. ........ A61M 31/00 |
| 2001/0046600 A1 | 11/2001 | Hsiao et al. |
| 2003/0163111 A1 | 8/2003 | Daellenbach |
| 2004/0030320 A1 | 2/2004 | Chee et al. |
| 2004/0035491 A1 | 2/2004 | Castellano |
| 2004/0162528 A1 | 8/2004 | Horvath et al. |
| 2005/0192530 A1 | 9/2005 | Castellano |
| 2005/0228225 A1 | 10/2005 | Hauschild et al. |
| 2006/0089631 A1 * | 4/2006 | Swanson ................ A61B 18/02 606/21 |
| 2006/0129125 A1 | 6/2006 | Copa et al. |
| 2007/0167921 A1 | 7/2007 | Burren et al. |
| 2007/0225554 A1 | 9/2007 | Maseda et al. |
| 2008/0114203 A1 | 5/2008 | Crank |
| 2008/0119784 A1 | 5/2008 | Roychowdhury et al. |
| 2008/0119823 A1 | 5/2008 | Crank |
| 2009/0124974 A1 | 5/2009 | Crank et al. |
| 2009/0312696 A1 | 12/2009 | Copa et al. |
| 2011/0015614 A1 | 1/2011 | Rykhus, Jr. et al. |

FOREIGN PATENT DOCUMENTS

| | | |
|---|---|---|
| WO | WO 00/40279 | 7/2000 |
| WO | WO 00/66199 | 11/2000 |
| WO | WO 01/36029 | 5/2001 |
| WO | WO 02/07812 | 1/2002 |
| WO | WO 2004/071612 | 8/2004 |
| WO | WO 2005/094921 | 10/2005 |
| WO | WO 2006/057604 | 6/2006 |
| WO | WO 2006/058426 | 6/2006 |
| WO | WO 2006/063180 | 6/2006 |
| WO | WO 2006/076699 | 7/2006 |
| WO | WO 2006/084821 | 8/2006 |
| WO | WO 2006/086719 | 8/2006 |
| WO | WO 2007/038591 | 4/2007 |
| WO | WO 2007/079152 | 7/2007 |
| WO | WO 2010/065126 | 6/2010 |
| WO | WO 2010/065127 | 6/2010 |
| WO | WO 2010/065133 | 6/2010 |
| WO | WO 2010/074705 | 7/2010 |
| WO | WO 2010/077271 | 7/2010 |
| WO | WO 2011/011423 | 1/2011 |

* cited by examiner

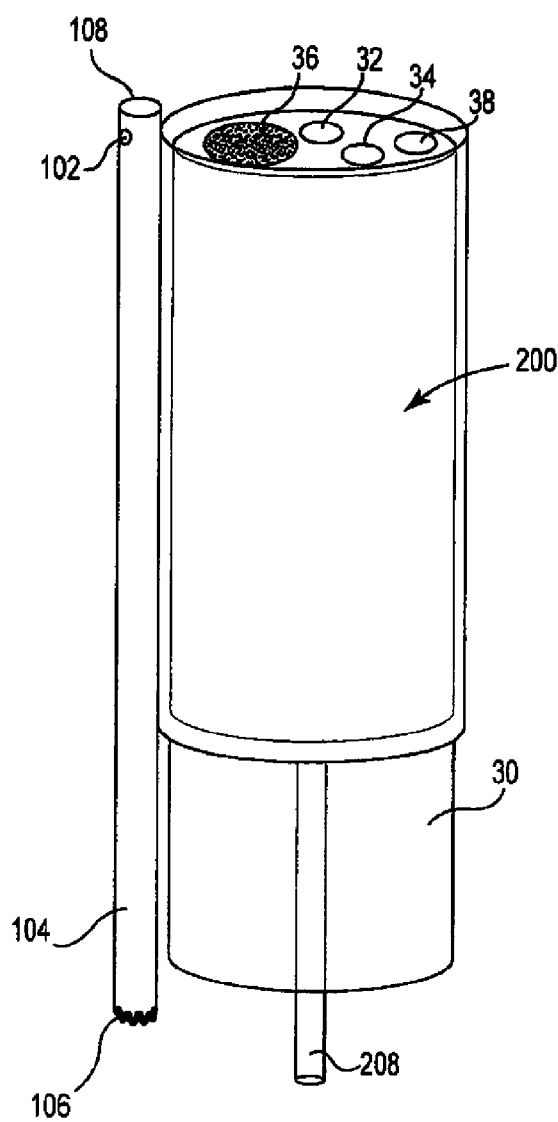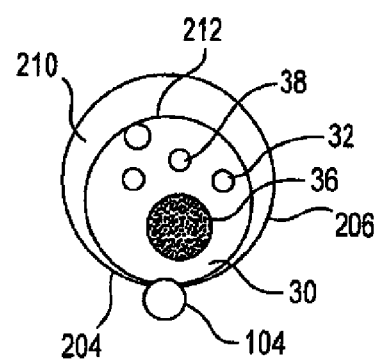
Fig. 3
Fig. 4

NEEDLELESS INJECTION DEVICE COMPONENTS, SYSTEMS, AND METHODS

PRIORITY CLAIM

This application is a continuation of U.S. patent application Ser. No. 13/133,125, which was filed on Jun. 6, 2011, which claims the benefit from International Application No. PCT/US2009/006384, which was filed on Dec. 4, 2009, which in turn claims priority under 35 USC §119(e) from provisional application Ser. No. 61/139,974, filed Dec. 22, 2008, by Crank, entitled ELASTIC ADAPTER FOR FLEXIBLE SCOPE COMPATIBLE INJECTION DEVICE; provisional application Ser. No. 61/122,808, filed Dec. 16, 2008, by Crank, entitled TWO-PIECE SIDE-FIRING JET INJECTION CATHETER; and provisional application Ser. No. 61/122,793, filed Dec. 16, 2008, by Crank, entitled URINARY TRACT CATHETER WITH SHAPEABLE TIP, each of these applications being incorporated herein by reference in its entirety.

FIELD OF THE INVENTION

The present invention relates generally to jet injection devices for the delivery of therapeutic fluids to a treatment site. Described device and method embodiments involve a fitting such as an elastic adapter or other removable or permanent fitting to attach to a distal end of a shaft. Exemplary elastic adapters can be elastically stretched to fit over a distal end of a flexible scope or other medical device shaft. Optionally and preferably an injection shaft such as a non-metal reinforced polymeric injection tube axially can be mounted alongside the fitting (e.g., elastic adapter) so as to be aligned parallel to the flexible scope. In other embodiments, an adapter can be attached to an injection shaft that is movably disposed within a lumen of a flexible scope or other medical device shaft.

BACKGROUND OF THE INVENTION

A wide variety of medical treatments are at least partially performed through the delivery and introduction of therapeutic compositions to a treatment location. In home or outpatient settings, typical delivery methods can comprise oral delivery, via liquid or solid forms, as well as a variety of inhalant style devices. In clinical or hospital settings, therapeutic fluids can be injected using needle based or in some minimally invasive procedures. The therapeutic fluid can be delivered through a tubular device such as a catheter or endoscope based systems.

One way in which therapeutic fluids can be delivered internally is through the use a tube-like device configured to provide a jet-injection of the therapeutic fluid at a desired treatment site. Generally, a remote injector is utilized to deliver the therapeutic fluid from an external reservoir located at a proximal end of the tube-like device so such administration can occur at a distal end of the tube-like device. Due to the relatively long travel length of the therapeutic fluid through the tube-like device, the remote injector must generally be capable of pressurizing the therapeutic fluid to pressures exceeding about 2,000 psi. In order to accommodate these pressures, the tube-like devices have been fabricated of alloys such as NiTi or stainless steel or with metal-reinforced polymers such as the braided tubes typically found in catheters.

Currently a number of manufacturers make a variety of flexible scopes to navigate the tortuous paths often found in the human body. Scopes such as cytoscopes, endoscopes, ureteroscopes, choledoscopes, and hysteroscopes vary slightly in size and shape by brand. There is advantage to using existing scopes for directing an injection device to a treatment site. Furthermore, there is advantage to controlling the overall size of the injection system and scope so as to minimize the invasiveness of the procedure.

SUMMARY OF THE INVENTION

The invention involves needleless fluid injection devices. These devices allow for localized delivery of therapeutic fluids that include biologically active species and agents such as chemical and biochemical agents at desired anatomical tissue locations including but not limited to locations in the male or female urinary tract, e.g., urethra, prostate, bladder, bladder neck, etc. Exemplary devices can be designed to deliver fluid at various tissue locations, optionally also multiple different therapeutic fluids or multiple different tissue locations.

Embodiments of exemplary devices include a tissue tensioner attached (removably or otherwise, such as through a removable or non-removable fitting) to a distal end of a shaft, which may be a working shaft or an injection shaft.

Other embodiments of exemplary devices include a fitting at a distal end of a shaft, e.g., a removable fitting or a non-removable fitting, to attach one distal end structure to another distal end structure. A fitting may be used, for example, to attach one distal end of a shaft (such as an injection shaft distal end) to another distal end of a shaft (such as a working shaft distal end). A distal end of a shaft may also optionally attach or be attached to a tissue tensioner optionally through the fitting or otherwise; the optional tissue tensioner may be associated with (e.g., integrally connected to or removably attached to) the fitting, or may be associated with the injection shaft or the working shaft apart from the fitting.

Still other exemplary embodiments include a tissue tensioner and a fitting in the form of a tissue tensioner assembly. The fitting may be a fitting that attaches to a distal end of a shaft (e.g., working shaft or injection shaft), removably or non-removably.

In slightly more detail, certain exemplary devices include a tissue tensioner assembly comprising a tissue tensioner and a fitting, wherein the fitting can be attached to a distal end of a shaft. The fitting can be attached to a shaft, such as an injection shaft or a working shaft, in a removable or a non-removable, e.g., semi-permanent or permanent, fashion. As used herein, a fitting is considered "removable" if the fitting can be attached to a shaft in a manner sufficiently secure to allow the fitting to remain securely attached to the shaft during an injection procedure without the fitting becoming undone, and the fitting can be removed from the shaft without permanently damaging the shaft or the fitting so at least one of the fitting or the shaft can be re-used.

In certain embodiments a tissue tensioner (e.g., as part of a tissue tensioner assembly) can be attached (removably or non-removably) to a distal end of an injection shaft, and the injection shaft can be inserted into a working lumen of a working shaft. Optionally a proximal end of the injection shaft can be inserted into a distal end of the working lumen (alternately a distal end of the injection shaft can be inserted into a proximal end of the working lumen) and the injection shaft can be placed within the length of the working lumen. A tissue tensioner assembly can be attached to the distal end of the injection shaft, before or after inserting the injection shaft into the working shaft. The tissue tensioner assembly may include an elongate actuating shaft, lumen, or mechanism that extends to a proximal end; a proximal end of this elongate shaft, lumen, or actuating mechanism can also be inserted into a distal end of the working lumen.

In alternate embodiment a tissue tensioner (e.g., in the form of a tissue tensioner assembly) can be attached to a distal end of a working shaft, such as by use of a fitting and in a removable or non-removable fashion. An injection shaft can be associated with the working shaft; for example an injection shaft can be secured adjacent to the working shaft, length-wise along an external surface of the working shaft, optionally by attachment to the same fitting that attaches to the working shaft and to the tissue tensioner. Alternately an injection shaft may be placed permanently, removably, integrally, securely, or movably, within a working shaft, such as but not necessarily within a working lumen.

Exemplary embodiments of described devices can include a non-metal, polymeric tube-like device (e.g., an "injection lumen") for delivering a therapeutic fluid to a treatment site within a patient, attached (removably or non-removably) at a distal end to an elastic adapter (or other type of removable "fitting," included but not limited to elastic adapters) sized to fit over a flexible scope (or "working shaft") distal end. An exemplary fitting can be an elastic adapter in the form of a sleeve-like device disposed about a distal end of the flexible scope. The exemplary elastic adapter may be manufactured from compliant or semi-compliant material. The elastic adapter has a diameter less than the outer diameter of the scope associated with the injection treatment. The needleless injection lumen (or "injection shaft") may be attached to the outer diameter of the elastic adapter or to an inner diameter with the injection port (or "injection orifice") disposed adjacent to an aperture (in the adapter). The elastic adapter may also include an upper rim to prevent the elastic adapter from axially sliding from the distal end of the scope.

In one embodiment, an elastic adapter may be a two layer device so as to include an inflation element (or "inflatable balloon" that can function as a "tissue tensioner"). An inner elastic sleeve comprises a first layer. The first layer is elastically mounted about the distal end of a flexible scope (e.g., working shaft). As the flexible scope is stiffer than the elastic adapter, the elastic tension created by the stretched elastic adapter does not impinge upon the scope. The second layer is attached around the outer diameter of the first layer to create a balloon. A balloon inflation lumen is disposed axially along a central aperture (of the working shaft) with a first end in communication with a media source such as compressed air or a fluid. A second end of the balloon inflation lumen is in communication with the space between the first and second layer. It is envisioned that the second layer may radially overlap the axial ends of the first layer. In this embodiment, the injection lumen may be attached to the second layer.

It is further envisioned that in some embodiments the second layer may only partially surround the first layer. For example, the second layer maybe disposed eccentrically around the first layer leaving an axial section of the first layer exposed. The injection lumen would thus be attached to the first layer along the exposed section. As the apposition balloon inflates the injection lumen can thus be positioned. The eccentric geometry allows the apposition balloon to force the injection lumen against the tissue chosen for treatment.

A non-metal, polymeric tube-like injection device (e.g., injection shaft) can be fabricated using suitable high strength polymers including, for example, polyimide, polyetherimide available from General Electric under the trade name Ultem® and linear aromatic polymers such as PEEK™ available from Victrex plc. In some embodiments, a non-metal, polymeric tube-like device can be reinforced through the inclusion of materials including nano-particles, clays and/or glass. In some presently contemplated embodiments, the non-metal, polymeric tube-like device can be reinforced with one or more polymers such as, for example, tubes braided with Kevlar or other high-strength polymers. The non-metal, polymeric tube-like device can be fabricated so as to have a burst strength exceeding at least about 200 pounds per square inch, e.g., exceeding 1,000 or 2,000 psi, and in some embodiments, having a burst strength within a range of about 2,000 psi to about 5,000 psi. The non-metal, polymeric tube-like device can be fabricated so as to have distention properties, wherein an orifice or jet port located at a distal end of the polymeric tube-like device retains its shape and/or size without suffering swelling that can have a detrimental impact on a fluid jet used to deliver the therapeutic fluid at the treatment site.

In one aspect the invention relates to a tissue tensioner assembly capable of being connected to an elongate shaft. The tissue tensioner assembly includes: a tissue tensioner comprising an expandable surface capable of exhibiting an expanded state and a non-expanded state, and a fitting connected to the tissue tensioner, the fitting capable of attaching the tissue tensioner to a shaft.

In another aspect the invention relates to an elongate shaft capable of injecting fluid into tissue. The shaft includes: a working shaft comprising a working shaft proximal end, a working shaft distal end, and a working lumen extending between the working shaft proximal end and the working shaft distal end; an injection shaft comprising an injection shaft proximal end and an injection shaft distal end, the injection shaft moveably disposed within the working lumen; and a tissue tensioner located at the injection shaft distal end, the tissue tensioner comprising an expandable surface capable of exhibiting an expanded state and a non-expanded state.

In yet another aspect the invention relates to an elongate shaft capable of injecting fluid into tissue. The shaft includes: a working shaft comprising a working shaft proximal end and a working shaft distal end, and an injection shaft comprising an injection shaft proximal end and an injection shaft distal end. The injection shaft distal end is attached to the working shaft distal end by a removable fitting.

In yet another aspect the invention relates to a method of connecting a working shaft distal end and an injection shaft distal end. The method includes: providing a fitting assembly comprising an injection shaft distal end and a removable fitting capable of being attached to a working shaft distal end, and attaching the removable fitting to the working shaft distal end.

In yet another aspect the invention relates to a method of assembling a shaft and tissue tensioner. The method includes: providing a tissue tensioner assembly comprising a tissue tensioner comprising an expandable surface capable of exhibiting an expanded state and a non-expanded state, and a fitting connected to the tissue tensioner; and attaching the fitting to an elongate shaft.

In another aspect the invention relates to a method of assembling a shaft and tissue tensioner. The method includes: providing an injection shaft comprising an injection shaft proximal end, an injection shaft distal end, and a tissue tensioner at the injection shaft distal end, the tissue tensioner comprising an expandable surface capable of exhibiting an expanded state and a non-expanded state; providing a working shaft comprising a working shaft distal end, a working shaft proximal end, and a working lumen extending between the working shaft distal end and the working shaft proximal end; and inserting the injection shaft proximal end into a distal end of the working lumen.

In another aspect the invention relates to a combination of two or more components of a needleless injection system selected from: a console, a removable pressure chamber, an injection shaft, a tissue tensioner, a fitting, and a working shaft.

The above summary of the various representative embodiments of the invention is not intended to describe each illustrated embodiment or every implementation of the invention. Rather, the embodiments are chosen and described so that others skilled in the art may appreciate and understand the principles and practices of the invention. The figures in the detailed description that follows more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 3 is an alternate two layer embodiment of an elastic adapter with a therapeutic fluid delivery system for delivering a therapeutic fluid disposed about a flexible scope according to the present disclosure.

FIG. 4 is a sectional view of the alternate embodiment of FIG. 3.

Figure 1:
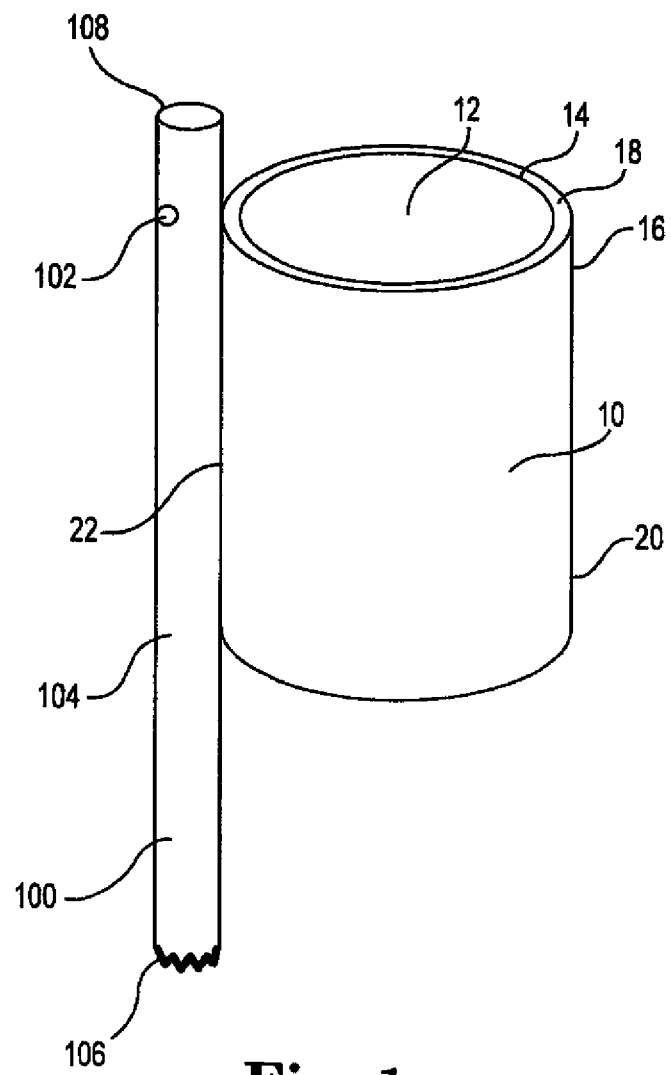
FIG. 1 is a perspective view of an embodiment of an elastic adapter with a therapeutic fluid delivery system for delivering a therapeutic fluid to a treatment location according to the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

DETAILED DESCRIPTION

In the following detailed description of the present invention, numerous specific details are set forth in order to provide a thorough understanding of the present invention. However, it will be obvious to one skilled in the art that the present invention may be practiced without these specific details. In other instances, well-known methods, procedures, and components have not been described in detail so as to not unnecessarily obscure aspects of the present invention.

The invention relates to devices comprising a shaft for injecting a fluid into tissue, such as a needleless injection device. Needleless devices as described generally include a distal end and a proximal end. As used herein, the "distal end" refers to a portion of the device that is located internally within a patient's body during a treatment procedure, generally including the distal end of an elongate shaft. A shaft distal end may include functional features that operate on fluid or tissue during use, such as one or more injection orifice, optional delivery head (end effector, nozzle, etc.) to house one or more injection orifices, optionally a tissue tensioner (as described), optionally a fitting to attach one component of a shaft distal end to one or more other component, optionally one or more of a light, optical feature, steering feature, etc. A "proximal end" of an exemplary needleless device can include an injector body or "console" that remains external to the patient during use. An exemplary console can include a housing that connects to or is otherwise (directly or indirectly) in fluid communication with the shaft. The console can include fluid that can be pressurized by a pressure source to cause the fluid to flow through the shaft for injection into tissue at the distal end.

A device can eject fluid from at least one injection orifice located at the distal end of the shaft. Optionally, multiple injection orifices may be located at one or more locations along a length of or about a circumference of a shaft distal end. Devices, systems, and methods as described can be used to inject fluid (sometimes referred to as an "injectate" or "injection fluid," which may be any type of fluid such as a therapeutic fluid) into tissue in a needleless manner whereby the injectate passes as a pressurized fluid stream (or "jet") through a surface of a tissue, penetrating without the use of a needle through the tissue surface and into the bulk of the tissue, and dispersing as particles or droplets within the tissue below the tissue surface. This contrasts with injections performed using a needle, whereby a hollow needle structure is used to penetrate tissue to locate a hollow end of the needle within a tissue mass, below the tissue surface, after which the needle carries fluid into the bulk of the tissue and delivers the fluid at a relatively low pressure to the tissue in the form of a body or pool of fluid known as a bolus.

A fluid stream or jet ejected for injection into tissue by a needleless injection system can be of a size (e.g., diameter), velocity, pressure, and volume to allow the fluid stream to penetrate directly through a tissue surface, then disperse within the tissue. The stream can be considered to be a relatively high velocity, high pressure, small diameter jet that after entry through a tissue surface disperses within the tissue, preferably as a multi-directional collection of particles (e.g., a "cloud") or droplets within the bulk of the tissue. Exemplary pressures of a fluid at a pressure chamber can be at least 200 pounds per square inch (psi), e.g., from 300 to 5000 pounds per square inch. Without limiting the scope of the present description: when injecting bladder tissue a pressure of from 250 to 1000 psi can be effective, measured at the pressure chamber; when injecting prostate tissue a pressure of from 3500 to 5000 psi can be effective, measured at the pressure chamber.

Exemplary needleless devices may be used for treating various physical ailments or conditions at any bodily tissue, for example to treat tissue that contains or is within reach of injection through a body cavity or body lumen, e.g., by accessing tissue through a body lumen, vessel, or cavity, and injecting tissue by placing an injection orifice within the lumen, vessel, or cavity. The type of tissue injected for treatment can be any amenable tissue, especially tissue accessible through a body lumen such as prostate tissue accessible through a urethra.

Exemplary needleless fluid delivery devices or systems can include a proximal end that includes a console, and an elongate shaft extending from a proximal end in communication with the console to a distal end. The elongate shaft can include an injection shaft and an injection lumen, optionally disposed permanently, semi-permanently, or loosely and movably within or adjacent to a working lumen. A distal end of the injection shaft can include one or more injection orifice fluid communication with the console, through an injection lumen.

A console generally can include a housing, a pressure chamber, and a pressure source. A console can be of any configuration, size, or design, ranging from a small, hand-held design to a relatively larger floor or table-mounted console. Optionally a console can include separate or separable components such as a pressure chamber (e.g. "connector member") that can be attached between a housing and a proximal shaft end, used for an injection procedure, and detached and optionally discarded. A shaft (e.g., an injection shaft or a working shaft) can also be attached to a console, pressure chamber, or connector member, in a manner to allow separation and optional re-attachment or disposal after one or more use. With separable components, a shaft or pressure chamber can be attached to a console housing and used to inject a first patient or a first injectate; the shaft or pressure chamber (e.g. "connector member") can then be discarded or sterilized. A second shaft or pressure chamber can be attached to the console to treat a second patient or the first patient with second injectate or another amount of the first injectate. The second patient or injectate can involve injection and treatment of the same type of tissue as the first patient or injectate, or of a new type of tissue (e.g., prostate or bladder). In this manner, separable and optionally disposable shaft or pressure chamber components of a needleless injection system can allow a console housing to be used multiple times to inject the same or different injectates, to the same or different patients, and to the same or different types of body tissue.

A console can include actuating features to control distal end features, e.g., for steering a steerable distal end of a steerable shaft, to actuate ejection of fluid, to move a moveable or extendable injection shaft or one or more injection orifice relative to another shaft component such as a working shaft, optional ports to connect a console housing to auxiliary devices, electronics such as controls, optic features such as a lens, fiber optic, or electronic viewing mechanism to allow viewing through an optical feature (to view a location of delivery), and an actuating mechanism or pressure source for a tissue tensioner in the form of a mechanical tissue tensioner or an inflatable balloon. One or more attachment ports can optionally attach a console to an external and optionally remote component such as an external or remote pressure source, vacuum source, or an external or remote fluid reservoir to supply injectate or other fluid, such as to inflate a balloon. For example, a console (e.g., console housing or connector member) may have a fluid port that attaches to a source of a fluid to supply the fluid to the console, such as to a permanent or detachable pressure chamber. Embodiments of consoles can include a permanent or removable pressure chamber and a pressure source capable of pressurizing a fluid contained in the pressure chamber to cause the fluid to flow from the console, through a lumen in the shaft, and then through an injection orifice.

A fluid chamber can be a space (volume) at a proximal end of a device such as at a console housing, useful to contain pressurized or non-pressurized fluid, such as injectate or a gaseous or liquid fluid to inflate a balloon (e.g., tissue tensioner). Examples of specific types of fluid chambers include fluid reservoirs and pressure chambers. Optionally a proximal end of a device may include one or multiple fluid reservoirs and pressure chambers.

A fluid reservoir is generally a type of fluid chamber that can contain a fluid for a purpose of containing, transferring, holding, or storing a fluid, such as a fixed volume fluid chamber, and may be included as a permanent or removable (attachable and detachable) component of a console.

A pressure chamber can be a type of fluid chamber for containing fluid (e.g., injectate) for a purpose of placing the fluid under pressure to deliver the fluid through a lumen to a distal end of a shaft for ejection from an ejection orifice. Examples of pressure chambers include a syringe chamber and other variable volume spaces that can be used to contain and pressurize a fluid. Examples of variable volume pressure chambers include spaces that can exhibit a variable volume based, e.g., on a plunger, piston, bellows, or other mechanism for increasing or decreasing the volume (and correspondingly decreasing or increasing pressure) within the variable volume chamber space. A pressure chamber can be pressurized by a pressure source attached to the plunger, bellows, or piston, etc., such that fluid contained in the pressure chamber is ejected under pressure, e.g., for priming a device, or for ejecting fluid from an ejection orifice for injection or to produce a control force. A pressure source may be any source of energy (e.g., mechanical, electrical, hydraulically derived, pneumatically derived, etc.) such as a spring, solenoid, compressed air, manual syringe, electric power, hydraulic, pneumatic pressure sources, etc. A pressure chamber may be a permanent or removable (attachable and detachable) component of a console.

Examples of consoles, console features and combinations of console features that can be useful according to the present description are identified in Assignee's U.S. Pat. No. 8,262,605; and in Assignee's following copending patent applications: U.S. Pat. Publ. Nos. 2009/0312696; 2011/0270216; 2011/0245762; and 2011/0264036, the entireties of these patent documents being incorporated herein by reference.

In communication with a proximal end of a device is an elongate shaft that extends from the proximal end (i.e., from a proximal shaft end), that is optionally removably connected to the console (or a component of the console such as, a removable pressure chamber), to a distal end that can be placed in a patient during an injection procedure. A shaft can be of various designs, minimally including an injection lumen to carry injectate from a proximal end of the device to a distal end of the injection shaft. Shafts for needleless devices as described are also described in Assignee's copending U.S. Pat. Publ. No. 2011/0282318.

An injection shaft minimally includes an injection lumen in communication with an injection orifice. The injection shaft can include structure such as sidewalls that define the injection lumen, the sidewalls being of sufficient strength to withstand operating pressures sufficient to deliver injectate from the injection orifice at an elevated pressure sufficient to cause the injectate to be ejected from the injection orifice to penetrate a tissue surface and become injected and into and dispersed below the tissue surface, as described herein. Exemplary elevated pressures ("injection pressures") may be at least 200, e.g. 1,000, or 2,000 pounds per square inch or greater as measured at the distal end of the injection lumen, or at the pressure chamber. An injection shaft may be of a flexible material (e.g., a metal or polymeric tube) that can withstand such injection pressure, and may be prepared from exemplary materials capable of withstanding pressure of an injection, e.g., nitinol, stainless steel, reinforced (e.g., braided) polymer, as also described elsewhere herein.

A basic version of a useful shaft as described can be an "injection shaft" that includes a proximal end, a distal end, a sidewall that defines an internal lumen ("injection lumen"), and at least one injection orifice at the distal end in connection with the injection lumen.

An injection shaft can be any elongate structure capable of delivering fluid to a distal end of the injection shaft at a pressure suitable to inject tissue, as described. Exemplary injection shaft structures include relatively flexible hollow bodies having a distal end, a proximal end, sidewalls extending between the ends, an internal lumen defined by interior surfaces of the sidewall. The injection lumen is in communication with one or more injection orifice at the distal end; the injection orifice may be as described herein, such as an aperture or bore in an injection shaft sidewall, an aperture or bore in a nozzle, end effector, injection head, or other structure in communication with the injection lumen.

An exemplary injection shaft can be in the form of a non-metal, polymeric tube-like device and can be fabricated using suitable high strength polymers including, for example, polyimide, polyetherimide available from General Electric under the trade name Ultem® and linear aromatic polymers such as PEEK™ available from Victrex plc for transporting the treatment fluid to the treatment area. In some embodiments, the non-metal, polymeric tube-like device can be reinforced through the inclusion of materials including nano-particles, clays and/or glass. In some presently contemplated embodiments, the non-metal, polymeric tube-like device can be reinforced with one or more polymers such as, for example, tubes braided with Kevlar or other high-strength polymers. The non-metal, polymeric tube-like device can be fabricated so as to have a burst strength exceeding at least about 200, e.g., 1,000 or 2,000 psi and in some embodiments, having a burst strength within a range of about 2,000 psi to about 5,000 psi. The non-metal, polymeric tube-like device can be fabricated so as to have distention properties, wherein one or more orifices or jet ports located at a distal end of the polymeric tube-like device retains its shape and/or size without suffering swelling that can have a detrimental impact on a fluid jet used to deliver the therapeutic fluid at the treatment site. See, e.g., U.S. Pat. Publ. No. 2008/0119823.

An exemplary injection shaft can include a sidewall that defines an outer shaft surface and an inner injector lumen, these being of continuous and relatively uniform dimensions of inner diameter, outer diameter, and wall thickness, along an entire length of the injection shaft. Alternately, an injection shaft, injector lumen, or sidewall, may change dimensions (e.g., wall thickness) along the length of the injection shaft, with a larger wall thickness (e.g., greater outer diameter) at a proximal end and a thinner wall thickness (e.g., reduced outer diameter) at the distal end. An example of an inner diameter of an injection shaft (i.e., a diameter of an injection lumen) can be greater than 0.020 inches, e.g., from 0.022 to 0.030 inches (for a lumen made of polyetheretherketone, or "PEEK"); exemplary outer diameters for the same exemplary injection shaft may be at least 0.032 inches e.g., from 0.034 to 0.045 inches. (An inner dimension of a fitting for placement on such an injection shaft may be, e.g., in the range from about 0.03 to about 0.05 inches.) A length of an injection shaft can be any length that functions to place a proximal end at a console and a distal end at a desired tissue location; exemplary lengths can be from as little as 15 inches if the console is a hand-held console, to as long as 100 inches if the console is floor based or table based.

An injection shaft can be a component of a shaft of a useful needleless injection device or system. Other shaft components may include additional elongate shaft structures with desired functionality, a single example being a device referred to herein as "medical device shaft" or a "working shaft," which can be used to securely or moveably support or house an injection shaft. For instance, an injection shaft can be incorporated permanently or movably (e.g., removably) against (alongside) or within (e.g., in a "working lumen" of) a working shaft. In exemplary embodiments an injection shaft can be loosely contained in a working lumen of a working shaft to allow movement of the injection shaft length-wise and rotationally relative to the working shaft; an injection shaft may be capable of moving longitudinally within a working lumen to allow the injection lumen to be extended distally from an open end of a working lumen at a distal end of the working shaft.

An example of a "working shaft" or "medical device shaft" can be a shaft that is useful in conjunction with an injection shaft, to manipulate and place the injection orifice of an injection shaft at a desired location for treatment of tissue. A "working shaft" or "medical device shaft" can function to support the injection shaft and can optionally and preferably include any of a variety of optional functionalities such as steerability, an optical function, a tissue tensioner, or combinations of these, in addition to supporting the injection shaft.

An example of a particularly preferred working shaft can include features of a typical cystoscope, endoscope, ureteroscope, choledoscope, hysteroscope, catheter (e.g., urinary catheter), or the like, or other similar type of medical device shaft, including one or more feature of flexibility, an optical function, a steerable distal shaft end, and a working lumen. A working lumen can be sized to loosely house or contain the injection shaft, preferably in a manner to allow the injection shaft to be moved lengthwise and rotationally within the working lumen, relative to the working lumen, such as to allow the injection lumen (and optionally an attached tissue tensioner) to be extended from an opening at a distal end of the working lumen, at a distal end of the working shaft. A typical diameter (or other dimension) of a working lumen extending along a length of a distal end of a working shaft can be in the range from about 1 to about 3 millimeters. A typical length of working shaft for placement of a distal end at a location of the urinary tract can be, e.g., from 15 to 25 centimeters. A typical outside diameter of a working shaft may be, for example, from about 4 to about 10 millimeters.

As used herein, the term "flexible shaft" refers to a shaft (e.g., an injection shaft or a working shaft) that is sufficiently pliable to allow bending and flexing that allow the shaft to be inserted through the meatus or an external incision, into the urethra or another body lumen, and to allow a portion of a distal end of the shaft to be guided into a body lumen or body cavity such as a urethra and optionally the bladder neck or bladder, as can be done with a Foley catheter. A flexible shaft can be sufficiently soft and pliable to conform or partially conform to a patient's anatomy, such as would a Foley-type catheter. A "steerable" shaft is a type of a flexible shaft having a distal end that can be maneuvered directionally (e.g., bent or curved) from a proximal end; steerable shaft distal ends are sometimes features of endoscopes and other medical device shafts.

Optionally, a shaft of a device as described may also be malleable, or "shapeable," meaning that a shaft distal end, or portion thereof, can be of a material capable of being shaped to a form, and to remain in that form during use, such as for insertion into a body lumen, until re-formed. A shaft or a shaft component, such as a working shaft or an injection shaft, can include a malleable component such as a bendable metal wire, coil, ribbon, tube, or the like, capable of being shaped, used without substantial deformation, and re-shaped. A malleable distal end can allow a distal end to be shaped by a user to assist in placement of the distal end through a body lumen such as a urinary tract, at a desired location. In some methods of treatment, there may be difficulties or challenges in passing a shaft distal end through a body lumen, or to place the distal end in contact with tissue for injection. A malleable shaft distal end, e.g., of an injection shaft in particular, e.g., used in conjunction with a working shaft within which the malleable injection shaft distal end is moveably disposed, or in conjunction with a working shaft adjacent to which the malleable injection shaft distal end is disposed, may assist in overcoming such potential difficulties. The malleable distal end tip may be formed by a user to a desired curve or bend, before or after placement in a working channel or adjacent to a working shaft; the working shaft may be inserted into a body lumen such as a urethra, and the formed, malleable injection shaft distal end may be extended from or placed adjacent to the working shaft with a shape that improves the ability to position the injection shaft or an injection orifice thereof, at tissue for injection. A shapeable portion may vary in stiffness, length, resilience, material, radiopacity, etc., and may be of any malleable material such as a polymer, metal, or polymer-metal composite.

A distal end of an injection shaft includes one or multiple injection orifices for ejecting fluid within a body of a patient. An injection orifice can be any form of opening, aperture, or orifice, such as an aperture or bore in an injection shaft sidewall, or an aperture or bore in a nozzle, end effector, injection head, or other structure in communication with an injection lumen. Injection orifices can be located at relative locations and orientations along a length or circumference of an injection shaft distal end to result in ejection and distribution of ejected fluid in different directions (e.g., circumferentially relative to the shaft), optionally or alternately at different distances along the length of the injection shaft. An injection orifice can be directed at any angle relative to a longitudinal axis of a shaft, such as perpendicular, angled toward a distal end, or angled toward a proximal end.

An injection orifice may have any useful size (e.g., length and diameter) to produce a fluid stream of ejected fluid that can penetrate a tissue surface to become injected into tissue. Examples of a useful range of diameter of an injection orifice may be from about 0.001 to 0.05 inches, e.g., from 0.001 to 0.010 inches, depending on factors such as desired injection parameters (injection depth, volume, pressure, exit velocity, etc.) and the type and size (e.g., depth) of tissue being injected. An injection orifice may be larger or smaller than an injection lumen leading to the injection orifice, if desired, to affect the exit velocity of the jet of injectate from the injection orifice. Examples of useful orifice shapes may include features such as a venturi, a continuous uniform diameter along the length of an orifice, a funnel-shape, etc.

According to exemplary injection methods and devices, an injection orifice may be located on a proximal side of a distal end tip at a location that allows the injection orifice and adjacent injection shaft sidewall to contact a tissue surface as a longitudinal axis of a shaft that contains the injection orifice is positioned in an orientation that is parallel to the tissue surface. These device embodiments are sometimes referred to as "side-fire" devices, herein. As used herein, a "distal end tip" can be considered a location of a distal end of an injection shaft that is the farthest (most distal) feature of the injection shaft distal end.

In certain embodiments of "side-fire" devices an injection orifice can be located a distance away from a distal end tip on a proximal side of the distal end tip so the injection orifice is located to contact tissue for injection by placing the shaft sidewall in contact with tissue. Examples of injection orifice locations for these embodiments can be locations along a distal end of a shaft that are in the range from about 1 to about 40 millimeters from the distal end tip, on a proximal side of the distal end tip, e.g., such as a distance in the range from about 1 to about 25 millimeters from the distal end tip.

According to certain exemplary devices, a distal end of a shaft (injection shaft, working shaft, or the like) can include a tissue tensioner, the tissue tensioner optionally being attached to the distal end of the shaft by a fitting that is attached to the tissue tensioner, such as as part of a tissue tensioner assembly. A tissue tensioner can be located at a distal end of a shaft, somewhat near to an injection orifice, e.g., to be within a body lumen such as a urethra, e.g., a prostatic urethra, and near the injection orifice when the distal end of the shaft is installed in a patient for injection. For example a tissue tensioner can be located at a lengthwise location along an injection shaft that is the same length-wise location as the length-wise location of an injection orifice.

A tissue tensioner can comprise an expandable surface, e.g., a continuous expandable surface such as an inflatable balloon, or a non-continuous expandable surface such as an expandable metal (or plastic) cage or the like. The expandable surface can exhibit an expanded state and a non-expanded state. According to exemplary methods, a tissue tensioner can be placed in a body lumen in a non-expanded state and expanded within the lumen to the expanded state. In the expanded state, the tissue tensioner contacts an internal surface of the lumen to hold the distal end of the shaft and an associated injection orifice in place relative to desired tissue for injection. The tissue tensioner can optionally produce tension or strain on the tissue in a manner that can affect the manner in which an injected fluid stream penetrates the tissue surface and becomes distributed in the tissue upon injection. A tissue tensioner can facilitate a good result upon injection of fluid through luminal tissue by ensuring that the luminal tissue is fixed and includes a desired amount of tension for receiving an injection.

Depending on the configuration of an injection orifice at a shaft of a device, or at an injector head, a tissue tensioner can be used to place a desired portion of tissue in (e.g., direct) contact with an injection orifice, i.e., a surface that contains an injection orifice. Alternately, a tissue tensioner can place a desired portion of tissue at a desired distance away from an injection orifice, e.g., in the instance of an injector head that includes two surfaces with a recessed surface including an injection orifice. The distance, if any, between an injection orifice and tissue, at injection, can be selected to affect properties of the injection, e.g., to affect the distance an injectate penetrates into tissue, the size of droplets formed beneath the tissue surface, and the pattern over which droplets of injectate are dispersed throughout tissue when injected. Other factors can also be adjusted to affect properties of the injection such as pressure and volume of injectate, size and shape of the injection orifice, etc.

Examples of tissue tensioners include inflatable balloons located at a shaft distal end near an injection orifice (e.g., at the same length-wise location as the injection orifice), and mechanically extendable structures such as paddles, protrusions, levers, metal or plastic cages, metal or plastic springs or spirals, and the like, any of which can be include a surface that can be extended (e.g., mechanically) from a distal end of a working shaft or injection shaft to place pressure on internal tissue, e.g., on urethral tissue within the prostatic urethra or other luminal tissue. Tissue tensioners, device shafts, and related mechanisms and methods are described in Applicants' copending U.S. Patent Publ. No. 2006-0129125 and U.S. Ser. No. 12/087,231, filed Jun. 27, 2008, by Copa et al., entitled DEVICES, SYSTEMS, AND RELATED METHODS FOR DELIVERY OF FLUID TO TISSUE, the entireties of both of these being incorporated herein by reference.

A balloon or a mechanically extendable tissue tensioner can be inflated or extended at a location that is approximately at a length along a distal end of a shaft that is near an injection orifice, e.g., at a length-wise location that is the same as the length-wise location of the injection orifice. When used within a lumen such as a urethra, the tissue tensioner can push luminal tissue (e.g., urethral tissue) away from the distal end of the shaft in a manner that causes the luminal tissue and an injection orifice to contact each other. This can be done, for example, by a balloon expanding from an opposite side of a shaft relative to an injection orifice to place pressure on luminal tissue located opposite from an injection orifice and to cause the injection orifice to contact adjacent luminal tissue, optionally to produce pressure, strain, or tension on the luminal tissue opposite of the balloon. A mechanical tensioner may be extended from a distal end of a shaft by use of an actuating mechanism such as a mechanical connection between the tissue tensioner and the proximal end of a device, such as at a working shaft proximal end. An inflatable balloon may be extended from a distal end of a shaft by inflating the balloon with pressurized fluid such as air or another gaseous or liquid fluid.

A distal end of a device as described may optionally include a fitting that functions to attach together two or more components of a distal end. Exemplary fittings can be any device or structure that engages and attaches to a distal end of an injection shaft or a working shaft. A fitting can be a component of or attached to another feature as described herein, such as a tissue tensioner, an injection shaft, or a working shaft.

Optionally, a fitting can be attached to an outer surface of an injection shaft or a working shaft; such a fitting can be in the form of a complete or partial ring or cylindrical surface that includes an interior dimension that fits around an outer surface (or portion thereof) of the injection shaft or working shaft.

Optionally, a surface of an injection shaft or a working shaft can include an opposing or complementary shape, form, or surface, that engages a shape or form of the fitting; examples of complementary or opposing surfaces can include opposing threaded surfaces; opposing snap-fit engagement elements; opposing elements of a mechanical detent engagement, a mechanical spring-engagement; a mechanical key-fit engagement, and the like. Other examples of fittings include opposing press-fit surfaces, and elastic band surfaces. These and like types of fittings can be prepared from plastic or metal materials. Elastic band fittings can be prepared from one or more elastic materials such as rubber (natural or synthetic), elastic polymer, silicone, latex, and the like.

Certain preferred embodiments of fittings can be orientation specific to allow an engagement at only a single orientation, e.g., a fitting may be "keyed. As a single example, a fitting in the form of a cylindrical or partially cylindrical receiver (or receptor) sized to engage a shaft may be keyed (opposing surface structures of the fitting and the shaft may allow engagement in only a single rotational orientation). A keyed fitting can be used to allow an engagement between two attached shaft elements to occur only at a desired orientation between elements of the shafts, e.g.: a fastener that attaches an injection shaft to a working shaft may be keyed to require desired orientation between an injection orifice of the injection shaft and the working shaft, for example to allow viewing of the injection shaft or injection orifice or to require desired positioning of the injection orifice relative to a tissue tensioner associated with the working shaft; alternately a fitting of a tissue tensioner assembly may be keyed to require placement of the tissue tensioner assembly at a desired orientation relative to a working shaft or an injection lumen (and injection orifice).

A fitting can be part of an assembly (e.g., a "fitting assembly") that includes the fitting removably or non-removably attached to another component such as a tissue tensioner, an injection shaft, or a working shaft. An example of a fitting assembly can be a fitting assembly that includes a fitting attached to an injection shaft distal end, wherein the fitting removably attaches to a working shaft. See FIG. 1. The fitting assembly can include one of any of the described fittings attached securely to the injection shaft, and situated to allow the fitting to be attached to a working shaft. Exemplary fittings include an elongate receptor that includes one or more of: threads; a snap-fit engagement; a mechanical detent engagement; a spring; a keyed engagement surface; or an elastic band, capable of being placed on a distal end of a working shaft. In use, the fitting assembly including the injection shaft distal end securely attached to the fitting assembly, can be removably attached to the distal end of the working shaft by attaching the fitting to the working shaft distal end. If desired, the fitting can be keyed to require a determined orientation between the working shaft and the injection shaft. If the fitting is an elastic band, the elastic band can be stretched over a working shaft distal end. Alternately, if the fitting is of a different type, such as a mechanical (threaded, etc.) fitting, the fitting can be attached mechanically. In injection methods, the fitting assembly can be removably attached to a distal end of a working shaft, the working shaft can be placed within a tissue lumen, an optional tissue tensioner can be expanded, fluid can be ejected from the injection shaft to inject tissue, the distal end of the working shaft can be removed from the patient, and the fitting assembly can be removed from the distal end of the working shaft. The working shaft can be re-used in later procedures, and the fitting assembly including the injection shaft may be disposed of or re-used. This embodiment of a fitting assembly can optionally include a tissue tensioner that becomes located about the working shaft distal end when the fitting assembly is placed on the working shaft distal end. See FIGS. 1 through 6.

Another example of a fitting assembly can be a fitting assembly that includes a tissue tensioner (i.e., a tissue tensioner assembly), and attached to a fitting, wherein the fitting can be removably or non-removably attached to an injection shaft distal end. The tissue tensioner assembly can include one of any of the described fittings attached securely to a tissue tensioner, and situated to allow the fitting to be attached to a distal end of a shaft such as a working shaft or an injection shaft. Exemplary fittings include an elongate receptor that includes one or more of: threads; a snap-fit engagement; a mechanical detent engagement; a spring; a keyed engagement surface; or an elastic band; capable of being placed on a distal end of a working shaft or injection shaft. If desired, the fitting can be keyed to require a pre-determined rotational orientation between the tissue tensioner and the working shaft or injection shaft. In use, the fitting of the tissue tensioner assembly can be removably (or non-removably) attached to the distal end of an injection shaft or a working shaft. If the fitting is an elastic band, for example, the elastic band can be placed (e.g., stretched) around the injection shaft distal end. See FIGS. 7A and 7B, showing such a tissue tensioner assembly removably attached to a distal end of an injection lumen.

A tissue tensioner assembly that includes a fitting that can be removably attached to a distal end of a working shaft can, in use, be used according to steps that include: removably attaching the tissue tensioner assembly to a distal end of a working shaft, placing the working shaft (the distal end of the shaft also being associated with an injection shaft) within a tissue lumen, expanding the tissue tensioner, ejecting fluid from an injection shaft associated with the working shaft to inject tissue, and removing the distal end of the working shaft from the patient. The tissue tensioner assembly can be removed from the distal end of the working shaft. The working shaft can be re-used in later procedures, and the tissue tensioner assembly may be disposed of or re-used. In this embodiment, the tissue tensioner assembly may optionally be securely attached to a distal end of an injection shaft and in use the injection shaft becomes disposed adjacent to an exterior surface, and along a length of, the working shaft.

A tissue tensioner assembly that includes a fitting that can be attached (removably or non-removably, such as by adhesive or by integral construction) to a distal end of an injection lumen can, in use, be used according to steps that include: placing the injection shaft within a working lumen of a working shaft such as by loading the proximal end of the injection shaft into the distal end of the working lumen or alternately by loading the distal end of the injection shaft into the proximal end of the working lumen, attaching the tissue tensioner assembly to a distal end of an injection shaft (optionally with the injection shaft already being loaded into the working lumen), placing the working shaft distal end (and injection shaft and tissue tensioner) within a tissue lumen, expanding the tissue tensioner, ejecting fluid from the injection shaft to inject tissue, and removing the distal end of the working shaft (and injection shaft and tissue tensioner assembly) from the patient. The tissue tensioner assembly can be removed from the distal end of the injection shaft; alternately, the entire injection shaft and tissue tensioner assembly can be removed from the working shaft. The working shaft can be re-used in later procedures, and the tissue tensioner assembly, working shaft, or both, may be disposed of or re-used.

Figure 7A:
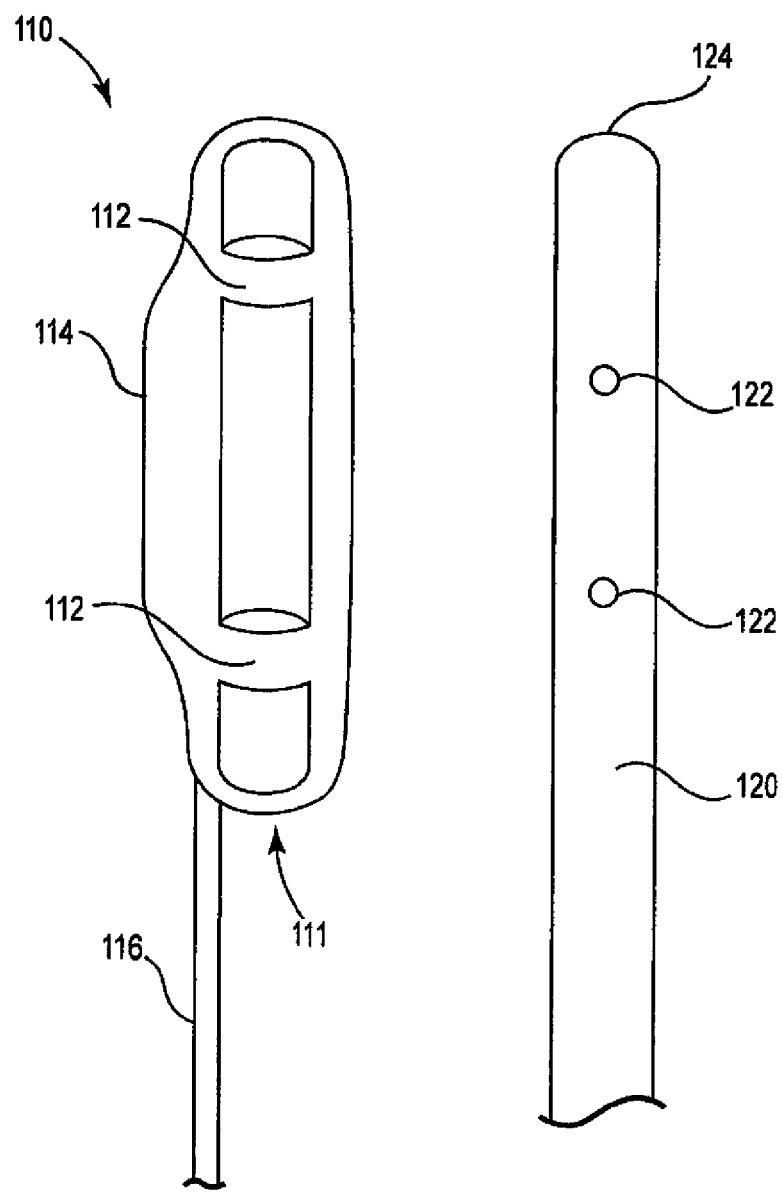
FIGS. 7A and 7B are side views of distal end components of shafts and assemblies as described.
Figure 7B:
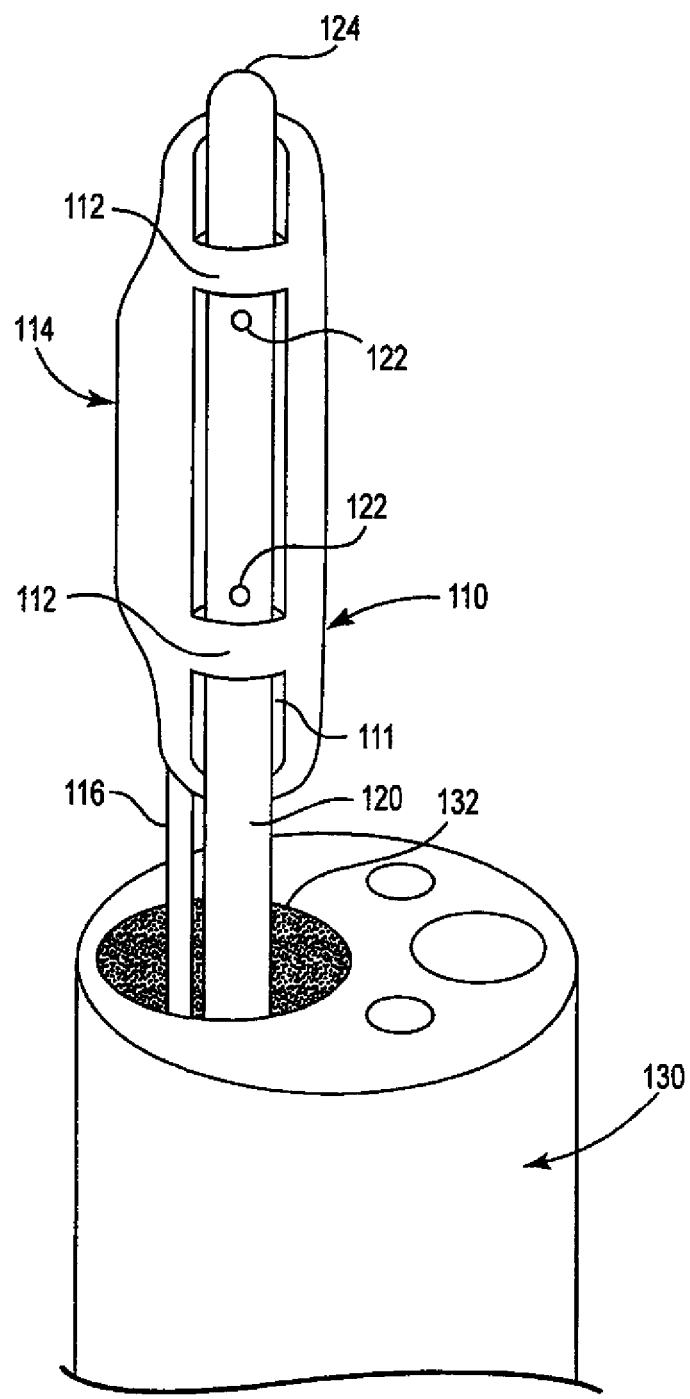

FIGS. 7A and 7B illustrate an embodiment of a tissue tensioner assembly. Assembly 110 includes fastener 111 that includes an elongate receptor sized to receive a distal end of injection shaft 120 (including injection orifices 122 and distal end tip 124). Rings or bands 112 can be elastic or non-elastic, plastic, metal, rubber, etc., bands to removably secure assembly 110 to the distal end of injection shaft 120. Tissue tensioner 114, illustrated as an inflatable balloon in a non-expanded state, is securely attached or optionally integral with fastener 111. Inflation lumen 116 is in fluid communication with tissue tensioner (balloon) 114 in a manner to allow gas or liquid fluid (e.g., air) to be inserted into tissue tensioner 114 to inflate and expand tissue tensioner 114. Optionally a proximal end of inflation lumen 116 can be accessible at the proximal end of a working lumen that can be associated with injection lumen 120 and tissue tensioner assembly 110.

Referring to FIG. 7B, assembly 110 is shown attached to a distal end of injection shaft 120, which is in turn disposed within working lumen 132 of working shaft 130. This distal end configuration comprising injection shaft 120, working shaft 130, and tissue tensioner assembly 110, is an example of a useful side-fire injection shaft configuration movably disposed within a working lumen. Side-firing injection orifices 122 are apposed by tissue tensioner (balloon) 114; when balloon 114 is expanded within a body lumen, side-firing injection orifices 122 are pressured against internal luminal tissue.

Still referring to FIGS. 7A and 7B, tissue tensioner 114 is an inflatable balloon but the tissue tensioner may alternately be of other types, such as an expandable cage. Also, fitting 111 is illustrated to be removable from injection shaft 120, but could alternately be permanent, semi-permanent, or non-removable, or could even be absent in that tissue tensioner 114 could optionally be integral with or otherwise attached to the distal end of injection shaft 120. In still alternate embodiments, inflation lumen 116 could be incorporated into injection shaft 120.

In injection methods, a distal end as shown in FIGS. 7A and 7B can be prepared by attaching the tissue tensioner assembly 110 (removably or permanently) to the distal end of injection shaft 120, as illustrated. The tissue tensioner assembly 110 and injection shaft 120 can be inserted into a distal end of working lumen 132 and passed through working lumen 132 to extend from the distal end of working lumen 132 to a proximal end (not shown) of working lumen 132. Working shaft 130 can be placed within a tissue lumen (e.g., urethra). Tissue tensioner 114 can be expanded to secure placement of injection orifices 122 against internal luminal tissue. Fluid can be ejected from injection orifices 122 to inject tissue. The distal end of working shaft 130 and injection shaft 120 can be removed from the patient. In embodiments wherein fitting 111 is removable, tissue tensioner assembly 110 can be removed from the distal end of injection shaft 120. Working shaft 130 can be re-used in later injection procedures. Injection shaft 120 may be removed from working lumen 132 and may optionally be re-used or discarded.

A needleless fluid delivery system 100 is illustrated generally in FIG. 1 as attached to elastic adapter (i.e., a fitting in the form of an elastic band) 10. The elastic adapter 10 is comprised of compliant or semi-complaint elastic material. The elastic adapter 10 defines a central aperture 12 through which a flexible scope (e.g., a working lumen) is inserted. The elastic adapter 10 has an inner face 14 and an outer face 16 separated by material thickness 18. It is envisioned that the elastic adapter 10 could be disposed about the distal end of a cystoscope, ureteroscope, choledoscope, endoscope or hysteroscope (e.g., any type of (working shaft). The amount of elastic tension about the flexible scope may be varied by selecting the thickness and/or type of the elastic material (and the size, e.g., inner diameter, of the elastic adapter). Furthermore, the axial length 20 of elastic adapter 10 may include designated bending areas or areas of greater elastic tension so as not to interfere with the efficiency of the flexible scope. The needless fluid delivery system 100 is attached to the elastic adapter 10 axially at connection region 22. In alternative embodiments it is envisioned that the needless fluid delivery system 100 may be connected by radial bands attached to the outer face 16 of the elastic adapter 10 or is disposed within central aperture 12 of the elastic adapter 10.

Needleless fluid delivery system 100 can comprise an injector (e.g., at a proximal end, not shown), an applicator lumen ("injection lumen") 104, and an injection orifice 102. The injector (e.g., including a console as described herein) can be as simple as manually activated syringe, or can comprise an automated injector including a user interface and a connector member. A connector member at a proximal end or other fluid chamber can include a therapeutic fluid supply and the user interface can comprise an input means for selectively delivering a pressurized fluid through the connector member. Representative input means can include foot pedal, switches, buttons or a touch-screen capable of receiving touch commands as well as displaying system information including a mode of operation as well as operating parameters. The applicator lumen 104 can comprise a non-metal, polymeric tube like device having a proximal attachment end 106 and a distal treatment end (or injection shaft distal end) 108. A non-metal, polymeric tube like device can have a tube length that corresponds to a type of treatment to be performed within a patient's body. For example, when a non-metal, polymeric tube like device is configured to perform a cystoscope or endoscopic procedure, the tube length can range from about 18 to about 72 inches in length. Once the distal treatment end 108, and more specifically, the administration orifice 102 is positioned with respect to the treatment location, the injector can be actuated so as to begin delivery of a therapeutic fluid. In positioning the needless fluid delivery system 100 at treatment location, it will be understood that a medical professional frequently employs a medical imaging system such as, for example, computer axial tomography (CAT), magnetic resonance imaging (MRI), or in the case of treatment of a prostate gland, an exemplary imaging means is transrectal ultrasound (TRUS) so as to achieve the desired position of administration Orifice 102. Another imaging means is by direct vision of the distal end of the inserted device, optionally the injection shaft or injection orifice, through direct vision by use of an endoscope.

Figure 2:
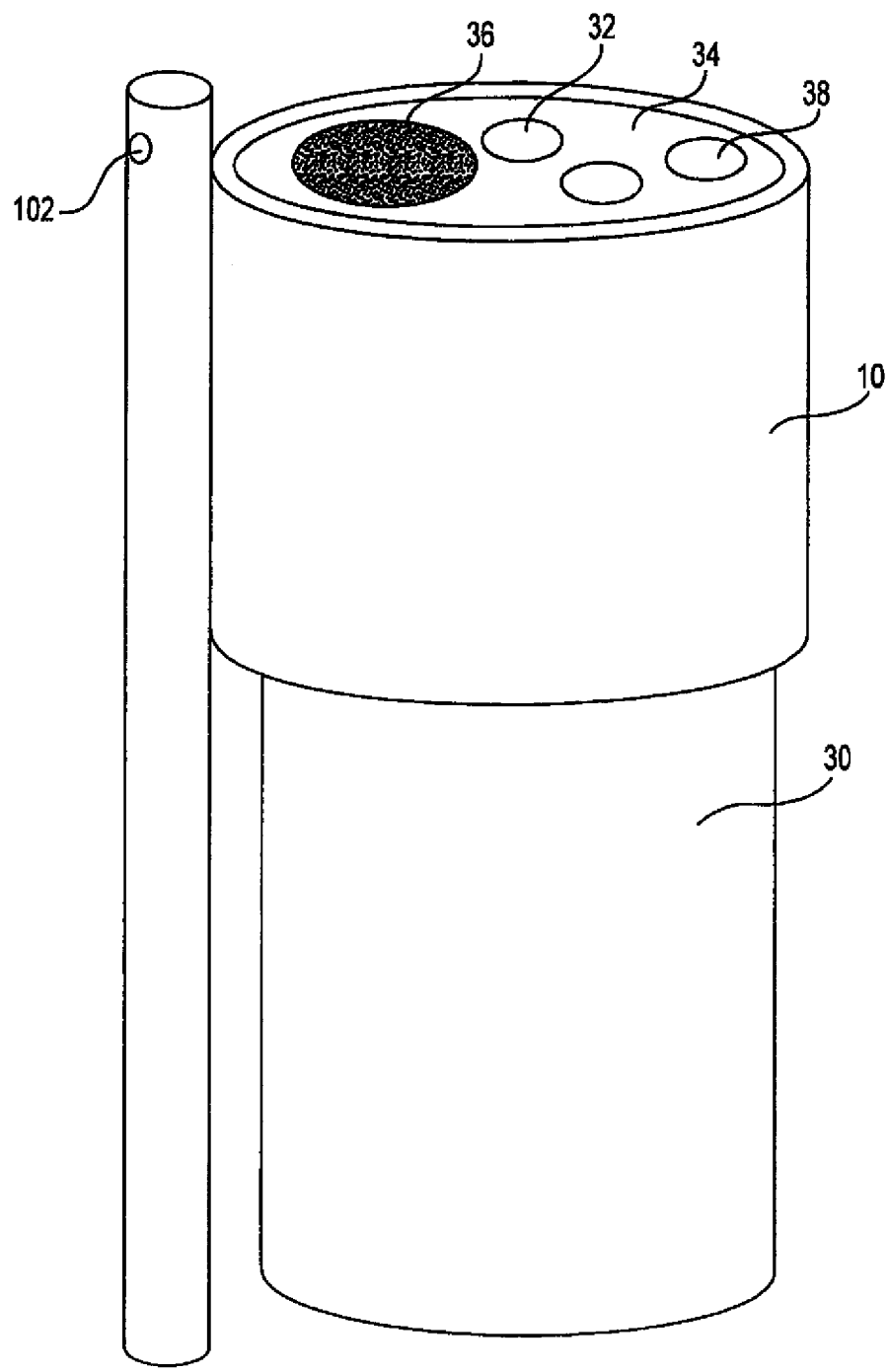
FIG. 2 is a perspective view of an embodiment of an elastic adapter with a therapeutic fluid delivery system disposed about a flexible scope according to the present disclosure.

As illustrated in FIG. 2, elastic adapter 10 is disposed about a flexible scope (e.g., working shaft) 30 such as a cystoscope to deliver therapeutic fluid to a treatment location, such as, for example, the urinary bladder, urethra, prostate, etc. Cystoscope 30 can include a working channel (working lumen) 36, a fiber optic light source 32 and lens 38 such that a medical professional can verify the distal treatment end 34 is positioned proximate the treatment location. It is envisioned that elastic adapter 10 could include an upper face that caps a portion of the distal treatment end 34 of the cystoscope 30. However, any cap portion must be positioned so as not to interfere with the cystoscope operation.

An alternate two-layer embodiment of an elastic adapter (or fitting) 200, is illustrated in FIGS. 3-6. A cystoscope 30 (or other working shaft) is positioned within elastic adapter 200 to deliver therapeutic fluid to a treatment location, such as, for example, the urinary bladder, urethra, prostate, etc. Cystoscope 30 can include a working channel (working lumen) 36, a fiber optic light source 32, and lens 38 such that a medical professional can verify the distal treatment end 34 is positioned proximate the treatment location. Needleless fluid delivery system 100 can comprise an injector (not shown), an applicator lumen ("injection lumen") 104, and an injection orifice 102.

The elastic adapter 200 may be a two layer device so as to include an inflation element 202. An inner elastic sleeve comprises a first layer 204. The first layer 204 is elastically mounted about the distal end 34 of the flexible scope 30. As the flexible scope 30 is stiffer than the elastic adapter 200, the elastic tension created by the stretched elastic adapter does not impinge upon the scope. The second layer 206 is attached around the outer diameter of the first layer 204 to create a balloon 210. A balloon inflation lumen 208 is disposed axially along a central aperture 212 with a first end (proximal end) in communication with a media source such as compressed air or a fluid. A second end 212 of the balloon inflation lumen 208 is in communication with the space between the first layer 204 and second layer 206. It is envisioned that the second layer 206 may radially overlap the axial ends of the first layer 204. The apposition balloon 210 is thus defined by the second layer 206 overlap of the first layer 204.

It is further envisioned that in some embodiments the second layer 206 may only partially surround the first layer 204 as illustrated in FIG. 4. For example, the second layer 206 maybe disposed eccentrically around the first layer 204 leaving an axial section of the first layer 204 exposed. The injection lumen (injection shaft) 104 would thus be attached to the first layer 204 along the exposed section. As the apposition balloon 210 inflates the injection lumen 104 can thus be positioned (within a body lumen). The eccentric geometry allows the apposition balloon 210 to force the injection lumen 104 against the tissue chosen for treatment.

Figure 5:
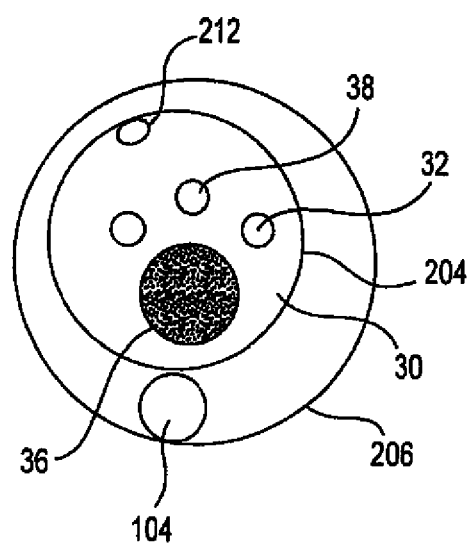
FIG. 5 is another alternate cross sectional view of the present invention.
Figure 6:
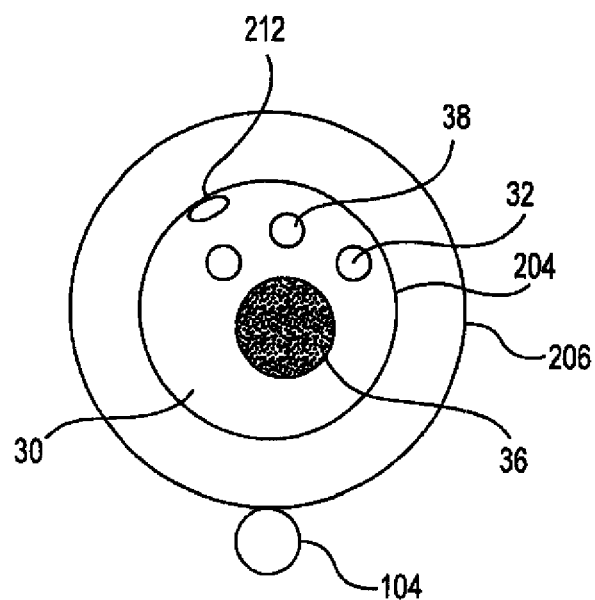
FIG. 6 is another alternate cross sectional view of the present invention.

In an additional embodiment, the injection lumen 104 would be attached between the first layer 204 and second layer 206, as illustrated in FIG. 5 or be attached to the second layer 206 as illustrated in FIG. 6.

In operation, the elastic adapter 200 would be placed about the distal end 34 of the flexible scope 30 by stretching the first layer 204. Elastic tension of the first layer 204 will maintain the position of the needleless injection system 100 relative to the flexible scope 30. The flexible scope 30 would be advanced to a treatment location at which time the balloon 210 would be filled through inflation lumen 212. Selectively inflating balloon 210 will assist in proper positioning of the injection orifice 102. Treatment may include providing a jet-injection of the therapeutic fluid through the injection orifice 102 at a desired treatment site. Generally, a remote injector is utilized to deliver the therapeutic fluid from an external reservoir located at a proximal end of the tube-like device 100. After treatment is complete, the balloon 210 is deflated and the flexible scope 30 withdrawn.

Figure 8:
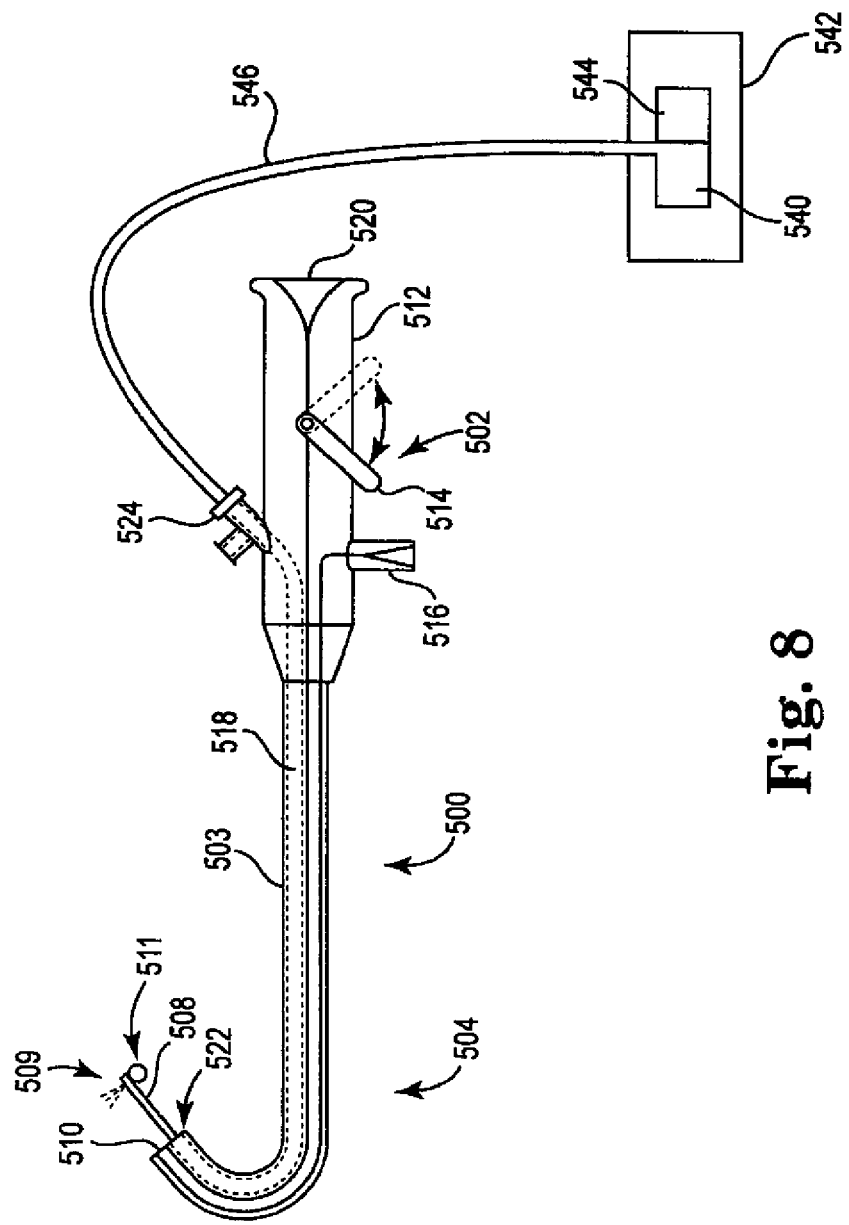
FIG. 8 is an illustration of an exemplary needleless injection system as described.

Another exemplary embodiment of a needleless injection system according to the present description is illustrated at FIG. 8. Device 500 includes a handle 502 and distal shaft end 504 of working shaft 503, which includes injection shaft 508 disposed within working lumen 518. The proximal end of the devices includes handle 502 of a scope that connects to working shaft 503 (e.g., of a cystoscope, endoscope, catheter, or other medical device shaft), including features useful for manipulating or operating features at distal end 504. Handle 502 includes: fiber optic light source 516; steering actuator 514, which can be manipulated to cause the steerable distal end of device 500 to move in at two or more dimensions); viewing lens 520 that allows viewing through fiber optic cable 510; and port 524, which allows for connection of a fluid source to handle 502. Articulation for steering of distal end 504 is indicated in dashed lines.

Still referring to FIG. 8, body 512 connects to working shaft 503, which includes lumens and mechanisms that connect features of proximal end handle 502 to distal end 504. Working lumen 518 is a hollow lumen or channel that extends within working shaft 503 and supports and contains injection shaft 508 in a manner that allows injection shaft 508 to move longitudinally along the length of working shaft 503, to allow the distal end of injection shaft 508 to extend from end opening 522 of working lumen 518. Working shaft 503 also includes fiber optic 510 and a steering mechanism (not shown) that allows steering (deflecting) of distal end 504 by movement of actuator 514. Light source 516 transmits light to distal end 504 by fiber optic 510.

Distal end 504 includes end opening 522 of working lumen 518 from which can be extended injection shaft 508, which includes at least one injection orifice. Also distal end 504 can be steered to allow movement of the tip of working shaft distal end 504, in coordination with extension of injection shaft 508, based on viewing through fiber optic 510, to deliver a fluid with accurate placement at a desired tissue location. The distal end of injection shaft 508 can be any design as described herein, e.g.: can include multiple injection orifices at different length-wise or circumferential locations; can include a tissue tensioner for apposition of an injection orifice against tissue; etc. As illustrated, fluid stream 509 is shown being ejected from an injection orifice (not shown); tissue tensioner (balloon) 511 is located on an opposite side of injection lumen 508 from the injection orifice.

While FIG. 8 illustrates an embodiment of a needleless injection system having an elongate shaft that includes an injection shaft disposed within a working lumen of a working shaft, other embodiments are alternately useful, such as embodiments of distal shaft ends of FIGS. 1 through 6, including an injection shaft dispose on an exterior of a working shaft, and an optional tissue tensioner disposed about a distal end of the working shaft.

Also illustrated at FIG. 8 is shaft 546 extending between port 524 of handle 502 and console 542. Console 542 includes pressure chamber 540 and pressure source 544.

With any of the above features of fluid delivery devices, a device could include an electronic process control system that can be programmed to make fluid deliveries having various locations, volumes, and other injection properties such as depth and degree (e.g., shape and distance) of dispersion and size of particles of fluid.

A needleless injection system can be use to perform treatment methods by steps that include one or more of the following: providing a needleless injection device substantially as described herein; inserting a distal end of a shaft of the fluid delivery device into a patient, e.g., through the meatus and into the urethra; navigating the distal end until an injection orifice at the distal end of the shaft is positioned at a desired delivery site. An injection shaft distal end can be positioned with a sidewall in contact with tissue, with a longitudinal axis of the shaft in line with (e.g., parallel to) tissue; an optional tissue tensioner can be used to cause a sidewall of the injection shaft distal end to contact and be pressed against the tissue surface to cause an injection orifice to contact the tissue surface for injection.

By any of the described methods, multiple injection orifices can provide the ability to place one or more different fluids at multiple locations of the urethra, prostate, bladder, or bladder neck, or other tissue, etc. Other treatment locations can include a rectal treatment location, a gastrointestinal treatment location, a nasal treatment location, a bronchial treatment location, or an esophageal treatment location. Features of devices described herein, such as optical features, steerable shafts, tissue tensioners, and the ability to deliver multiple different types of fluid, allow for improved control over the location of injection or instillation of a fluid.

According to certain exemplary fluid delivery procedures of the invention, fluid such as ethanol or a biologically active agent can be delivered to the bladder, urethra, prostate, or bladder neck, etc., in a manner that causes the fluid to be injected into the tissue using a needleless delivery orifice.

Devices of the present description can be useful to treat of various tissues, including of the urinary tract, in females or males. For example, devices as described may be useful to inject the bladder, bladder neck, the urethral tissue itself or the external sphincter, or for transurethral injection of the prostate in a male. In other embodiments, a fluid may be injected into tissue of the urinary tract (e.g., bladder, urethra, kidneys, ureters, prostate, etc.) such as individual or combination treatments using drugs or other therapeutic agents, e.g., botulinum toxin ("botox"), an antiandrogen, a neurotoxin, among others as will be understood. One advantage of injection of an active pharmaceutical agent at a location of use is the placement of the agent to avoid systemic side effects. Specific examples of active pharmaceutical agents that may be injected include botulinum toxin types A through G; 5-alpha reductase inhibitors such as dutasteride and finasteride; alpha blockers such as alfuzosin, doxazosin, prazosin, tamsulosin hydrochloride, terazosin, ethanol, to treat BPH; or any of various antibiotics (e.g., to treat prostatitis) and analgesics.

Figure 9:
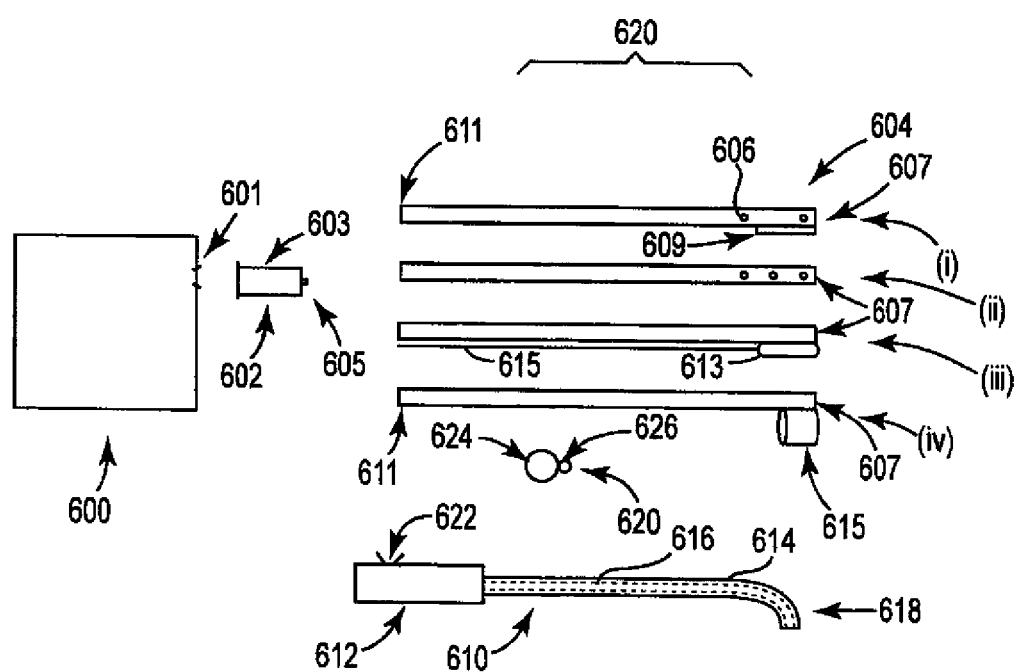
FIG. 9 illustrates options of combinations of systems as described.

FIG. 9 illustrates components of combination 620 of the invention. Any different combination of components can be included in a system or set. The components include console 600, optional "connector member" or external, removable pressure chamber 602, multiple varieties of injection shaft attachments (i) through (iv) that can be separately attached to console 600 or removable pressure chamber 602, and a single working shaft 610 including handle 612. Console or console housing 600 can be as described, and includes at least a pressure source. Port 601 allows connection to optional removable pressure chamber 602, which can be connected at a proximal end to port 601, and has distal end 605 that can be connected to a proximal end of an injection shaft attachment. Optional port 603 of pressure chamber 602 can be used to insert fluid into pressure chamber 602. Each of injection shaft attachments (i), (ii), (iii), and (iv), is exemplary and for purposes of illustration of exemplary combinations. Each includes a proximal end (611) that can removably attach to console or console housing 600, optionally by removably attaching to connector member 602 at distal end 605. Each injection shaft attachment also includes one or more injection orifice 606 at a distal end 604, connected through an inflation lumen (not shown) to the proximal end. Each injection orifice as illustrated is on a proximal side of a distal end tip 607.

An optional component of combination 620 is working shaft 610, which may be as described herein, e.g., including handle 612, port 622 suitable to introduce an injection shaft into working lumen 616 of working shaft 614, optional steerable distal end 618, and an optional optical feature (not shown).

Another optional component of a combination 620 can be a fastener assembly 620 having fastener 624 (e.g., an elastic fastener or other form of elongate receptor, optionally keyed) capable of attaching to a distal end of working shaft 624, and another fastener 626 (e.g., an elastic fastener or other form of elongate receptor, optionally keyed) capable of attaching to a distal end of an injection shaft.

A combination can include any one or combination of injection shaft attachments as shown or otherwise described herein. An exemplary injection shaft attachment can include any one or more of: a side-fire distal end with an elongate receptor 609 that may be an elongate elastic receptor or a non-elastic elongate receptor capable of attaching to an outside surface of working shaft distal end 618, and that is also removably attached to distal end 604 (i); a side-fire distal end with an optional malleable distal end feature (not shown) and multiple injection orifices along a length of the distal end (ii); a distal end with a single injection orifice near distal end tip 607, including tissue tensioner (e.g., inflatable balloon) 613 attached (e.g., securely) to the injection shaft distal end on the side opposite the injection orifice, and inflation lumen (or mechanical actuator, if the tissue tensioner is mechanically actuated) 615 extending alongside the injection shaft to a proximal end (iii); and, a distal end with a single injection orifice near distal end tip 607, including combined fitting and tissue tensioner 615 attached (e.g., securely) to the injection shaft distal end on the side opposite the injection orifice, an inflation lumen (not shown) extending alongside or within the injection shaft to a proximal end, and the combined fitting and tissue tensioner being an elastic or non-elastic fitting sized to fit at the distal end 618 of working shaft 614.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives.

The invention claimed is:

1. An elongate shaft capable of injecting fluid into tissue, the elongate shaft comprising:
    a working shaft comprising a working shaft proximal end, a working shaft distal end, and a working lumen extending between the working shaft proximal end and the working shaft distal end,
    an injection shaft comprising an injection shaft proximal end, an injection shaft distal end, and at least one needless injection orifice disposed through the sidewall at the injection shaft distal end, the injection shaft moveably disposed within the working lumen,
    a tissue tensioner removably secured to an outer surface of the injection shaft at the injection shaft distal end and moveable relative to the working lumen, the tissue tensioner comprising an expandable surface capable of exhibiting an expanded state and a non-expanded state, the tissue tensioner in the expanded state being capable of tensioning luminal tissue for injection by the needless injection orifice; and
    an inflation lumen in communication with the tissue tensioner.

2. The elongate shaft according to claim 1, wherein the tissue tensioner is secured to the injection shaft distal end by an adhesive.

3. The elongate shaft according to claim 1, wherein the tissue tensioner is secured to the injection shaft distal end by at least one elastic band.

4. The elongate shaft according to claim 1, wherein the tissue tensioner comprises an inflatable balloon and wherein the inflation lumen is in communication with the inflatable balloon.

5. The elongate shaft according to claim 1, wherein the working shaft comprises a steerable distal end.

6. The elongate shaft according to claim 1, wherein the needless injection orifice is located along a length of the injection shaft distal end at a distance in the range from about 1 to about 40 millimeters on a proximal side of a distal end tip.

7. The elongate shaft according to claim 1, wherein the injection shaft comprises an injection lumen extending between the injection shaft proximal end and the injection shaft distal end, the injection lumen being in fluid communication with the needless injection orifice and wherein the injection lumen is capable of withstanding a pressure of at least 200 pounds per square inch.

8. A method of placing an elongate shaft distal end of a needless injection device in a body lumen, the method comprising:
    providing a tissue tensioner assembly, the tissue tensioner assembly capable of being connected to the elongate shaft of the needleless injection device, the tissue tensioner assembly comprising:
        a tissue tensioner comprising an expandable surface capable of exhibiting an expanded state and a non-expanded state, and
        a fitting connected to the tissue tensioner, the fitting capable of attaching the tissue tensioner to the distal end of the elongate shaft at a location to allow the tissue tensioner in the expanded state to tension luminal tissue for injection by a needleless injection orifice of the needless injection device;
    attaching the fitting of the tissue tensioner to an outer surface of the distal end of the elongate shaft;
    placing the shaft distal end in a body lumen with the tissue tensioner in the non-expanded state, and
    expanding the tissue tensioner within the body lumen.

9. The method according to claim 8, wherein the step of expanding the tissue tensioner within the body lumen moves the needless injection orifice towards body tissue to be injected.

10. The method according to claim 8, wherein the tissue tensioner is secured to the elongate shaft distal end by an adhesive.

11. The method according to claim 8, wherein the tissue tensioner is secured to the elongate shaft distal end by at least one elastic band.

12. The method according to claim 8, wherein the tissue tensioner comprises an inflatable balloon and further comprises an inflation lumen in communication with the inflatable balloon.

13. A method of injecting tissue, the method comprising:
    providing an elongate shaft comprising:
        a working shaft having a working shaft proximal end, a working shaft distal end, and a working lumen extending between the working shaft proximal end and the working shaft distal end,
        an injection shaft comprising an injection shaft proximal end, an injection shaft distal end, and at least one needless injection orifice disposed through the sidewall at the injection shaft distal end, the injection shaft moveably disposed within the working lumen, and
        a tissue tensioner removably secured to the injection shaft at the injection shaft distal end and moveable relative to the working lumen, the tissue tensioner comprising an expandable surface capable of exhibiting an expanded state and a non-expanded state, the tissue tensioner in the expanded state being capable of tensioning luminal tissue for injection by the needless injection orifice;
    placing the shaft distal end in a body lumen with the tissue tensioner in the non-expanded state;
    expanding the tissue tensioner within the body lumen, and
    ejecting a fluid stream from the injection orifice such that the injection stream penetrates tissue.

14. The method according to claim 13, wherein the step of expanding the tissue tensioner within the body lumen moves the needless injection orifice towards the tissue to be injected.

15. The method according to claim 13, wherein the tissue tensioner is secured to the injection shaft distal end by an adhesive.

16. The method according to claim 13, wherein the tissue tensioner is removably secured to the injection shaft distal end by at least one elastic band.

17. The method according to claim 13, wherein the tissue tensioner comprises an inflatable balloon and further comprises an inflation lumen in communication with the inflatable balloon.

18. The method according to claim 13, wherein the working shaft comprises a steerable distal end.

19. The method according to claim 13, wherein the at least one needless injection orifice is located along a length of the injection shaft distal end at a distance in the range from about 1 to about 40 millimeters on a proximal side of a distal end tip.

20. The method according to claim 13, wherein the injection shaft comprises an injection lumen extending between the injection shaft proximal end and the injection shaft distal end, the injection lumen being in fluid communication with the needless injection orifice and wherein the injection lumen is capable of withstanding a pressure of at least 200 pounds per square inch.

\* \* \* \* \*